(12) United States Patent
Meininghaus

(10) Patent No.: US 6,828,389 B2
(45) Date of Patent: Dec. 7, 2004

(54) METHOD FOR PRODUCING POLYMER-BONDED 2-CHLOROTRITYL-CHLORIDE

(75) Inventor: Carsten Meininghaus, Schweiz (CH)

(73) Assignee: Lonza AG, Basel (CH)

( * ) Notice: Subject to any disclaimer, the term of this patent is extended or adjusted under 35 U.S.C. 154(b) by 73 days.

(21) Appl. No.: 10/275,268

(22) PCT Filed: May 11, 2001

(86) PCT No.: PCT/EP01/05416

§ 371 (c)(1),
(2), (4) Date: Nov. 12, 2002

(87) PCT Pub. No.: WO01/85758

PCT Pub. Date: Nov. 15, 2001

(65) Prior Publication Data

US 2003/0092847 A1 May 15, 2003

(30) Foreign Application Priority Data

May 12, 2000 (EP) .............................. 00110039

(51) Int. Cl.$^7$ .................................. C08F 8/18
(52) U.S. Cl. ................. 525/355; 525/333.3; 525/333.4
(58) Field of Search ............................ 525/355, 333.3, 525/333.4

(56) References Cited

U.S. PATENT DOCUMENTS

| 4,346,187 A | 8/1982 | Nichols |
| 5,198,531 A | 3/1993 | Webber et al. |
| 5,563,220 A | 10/1996 | Webber et al. |

FOREIGN PATENT DOCUMENTS

| WO | 92-22591 | 12/1992 |

OTHER PUBLICATIONS

Harre et al., "An efficient method for activation and recyclingof trityl resins", Reactive & Functional Polymers. 41, 111–114(1999).*

Copy of International Search Report from applicants's corresponding International (PCT) application.

Patent Abstracts of Japan, vol. 199, No. 612, (Dec. 26, 1996).

Patent Abstracts of Japan, vol. 011, No. 246 (C–439), (Aug. 11, 1987).

* cited by examiner

*Primary Examiner*—Ling-Siu Choi
(74) *Attorney, Agent, or Firm*—Fisher, Christen & Sabol

(57) ABSTRACT

A method for producing polymer-bound 2-chlorotrityl chloride of the formula (I):

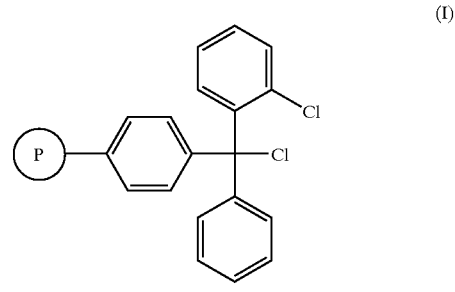

wherein

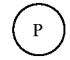

is a polymer support, preferably cross-linked polystyrene, by reacting a corresponding carboxylic acid with hydrogen chloride. The method enables the support resin from the solid-phase peptide synthesis produced after the splitting off of the peptide to be reused.

11 Claims, No Drawings

METHOD FOR PRODUCING POLYMER-BONDED 2-CHLOROTRITYL-CHLORIDE

This is a 371 of International (PCT) Application Number PCT/EP01/05416, filed on May 11, 2001, that has priority benefit of European Patent Application No. 00110039.5, filed on May 12, 2000.

The invention relates to a process for the preparation of polymer-bound 2-chlorotrityl chloride of the formula

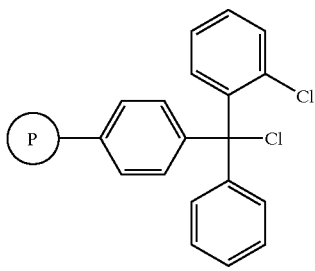

(I)

in which the symbol

is a polymeric support and preferably a crosslinked polystyrene resin.

Polymer-bound 2-chlorotrityl chloride is a commercially obtainable (Calbiochem-Novabiochem AG, Läufelfingen, Switzerland, Product No. 01-64-0021) reagent for the solid-phase synthesis of peptides. It is reacted here firstly with an N-protected amino acid, which forms the C-terminus of the peptide to be synthesized, to give the corresponding trityl ester. After synthesis of the peptide chain, the peptide is cleaved by treatment with a carboxylic acid, for example dilute trifluoroacetic acid or acetic acid, the corresponding polymer-bound trityl ester of the formula

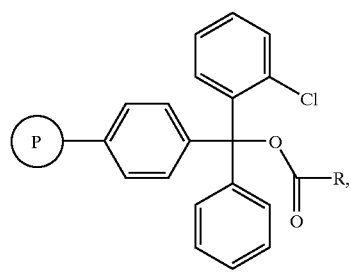

(II)

in which R is a $C_{1-4}$-alkyl or $C_{1-4}$-haloalkyl group and preferably methyl or trifluoromethyl being formed. The resin is thus consumed and can no longer be employed for further syntheses in this form.

$C_{1-4}$-Alkyl is to be understood here and below as meaning all alkyl groups having 1 to 4 carbon atoms, that is methyl, ethyl, propyl, isopropyl, butyl, isobutyl, sec-butyl and tert-butyl. $C_{1-4}$-Haloalkyl is correspondingly to be understood as meaning all $C_{1-4}$-alkyl groups having one or more identical or different halogen atoms as substituents, preferably perfluorinated $C_{1-4}$-alkyl groups such as trifluoromethyl.

The object of the present invention was therefore to make available a process which regenerates the polymer-bound 2-chlorotrityl chloride again from the acyloxylated resin (II) formed after cleavage of the peptide, which can then be used again for peptide syntheses.

According to the invention, this object is achieved by the process according to the invention.

It has been found that by simple treatment of the acyloxylated resin (II) with hydrogen chloride in an organic solvent the polymer-bound 2-chlorotrityl chloride (I) can be regenerated. Since the replacement of carboxylate by chloride is obviously an equilibrium reaction, the treatment is advantageously repeated a number of times using fresh solvent in order to remove the released carboxylic acid from the system and thus to achieve a complete replacement. It is also possible to percolate a packing of the acyloxylated resin (II) with a solution of hydrogen chloride until the carboxylate is completely replaced by chloride.

A suitable solvent is fundamentally any anhydrous organic solvent which does not react with hydrogen chloride and has an adequate solvent power for this. Preferably, dichloromethane is employed as the solvent.

The process according to the invention can be carried out both using a prepared solution of hydrogen chloride and using a solution produced in situ by passing gaseous hydrogen chloride into a reactor charged with the solvent and the acyloxylated resin (II).

The following example clarifies the implementation of the process according to the invention, without a restriction being seen therein.

EXAMPLE 5 g of trifluoroacetoxylated resin (II) were added to a double-jacketed reactor for solid-phase peptide synthesis (cylindrical glass vessel having a temperature-controlled jacket and glass frit in the lower part) and treated with 20 ml of dichloromethane. Nitrogen was firstly passed through the frit for 10 min and the arrangement was cooled to 5° C. A gentle stream of hydrogen chloride was then passed through the frit, the excess hydrogen chloride escaping from the reactor being absorbed in wash bottles containing sodium hydroxide solution. After about 10 min, the solution was filtered off with suction and replaced by fresh dichloromethane. Hydrogen chloride was then again passed in for about 10 min. This process was carried out a total of five times. The resin was then filtered off with suction under nitrogen and dried overnight at 30° C. The polymer-bound 2-chlorotrityl chloride thus obtained exhibited no significant differences in the binding capacity for amino acids to the commercially obtainable product.

What is claimed is:
1. A process for the preparation of polymer-bound 2-chlorotrityl chloride of formula:

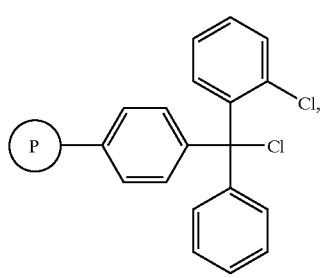

(I)

in which

is a polymeric support, comprising treating a corresponding carboxylic acid ester of the formula:

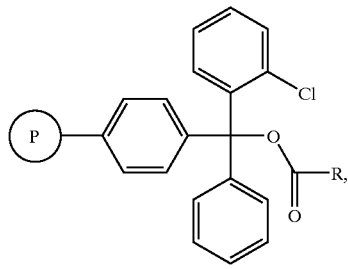

in which R is a $C_{1-4}$-alkyl or $C_{1-4}$-haloalkyl, with a solution of hydrogen chloride in an organic solvent.

2. The process according to claim 1, wherein R is methyl or trifluoromethyl.

3. The process according to claim 1, wherein the organic solvent used is dichloromethane.

4. The process according to claim 3, wherein the treatment is repeated a number of times with fresh solution.

5. The process according to claim 4, wherein the solution of hydrogen chloride in the organic solvent is prepared in situ by passing in hydrogen chloride gas.

6. The process according to claim 3, wherein a packing of the polymer-bond carboxylic acid trityl ester (II) is percolated with the solution of hydrogen chloride in the organic solvent.

7. The process according to claim 1, wherein the polymer support is crosslinked polystyrene.

8. The process according to claim 1, wherein the organic solvent used is dichloromethane.

9. The process according to claim 1, wherein the treatment is repeated a number of times with fresh solution.

10. The process according to claim 1, wherein the solution of hydrogen chloride in the organic solvent is prepared in situ by passing in hydrogen chloride gas.

11. The process according to claim 1, wherein a packing of the polymer-bound carboxylic acid trityl ester (II) is percolated with the solution of hydrogen chloride in the organic solvent.

* * * * *